(12) United States Patent
Fischer et al.

(10) Patent No.: US 6,402,514 B1
(45) Date of Patent: Jun. 11, 2002

(54) DENTAL WEDGE WITH ELASTOMERIC SIDES FOR ENHANCED RETENTION

(75) Inventors: Dan E. Fischer; Bruce S. McLean, both of Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/897,563

(22) Filed: Jul. 2, 2001

Related U.S. Application Data (63) Continuation-in-part of application No. 09/707,183, filed on Mar. 19, 2001.

(51) Int. Cl.[7] .................................................. A61C 7/00
(52) U.S. Cl. ...................................................... 433/149
(58) Field of Search ................................. 433/149, 148, 433/39

(56) References Cited

U.S. PATENT DOCUMENTS

| | | | |
|---|---|---|---|
| 109,665 A | 11/1870 | Richards | |
| 350,150 A | 10/1886 | Parr | |
| 421,925 A | 2/1890 | Graves | |
| 523,136 A | 7/1894 | Trakofler | |
| 1,529,075 A | 3/1925 | McIntyre | |
| 1,657,497 A | 1/1928 | Cichon | |
| 2,083,131 A | 6/1937 | Tornebohm | 206/16 |
| 2,150,005 A | 3/1939 | McNinch | 433/149 |
| 2,867,905 A | * 1/1959 | Meacham | 433/149 |
| 3,193,094 A | 7/1965 | Schulstad | 433/149 |
| 3,473,226 A | 10/1969 | Arlers et al. | 433/149 |
| 3,510,948 A | 5/1970 | Walthall | 433/149 |
| 3,590,814 A | * 7/1971 | Bennett | |
| 3,636,631 A | 1/1972 | Tofflemire | 32/64 |
| 3,815,243 A | 6/1974 | Eames | 433/149 |
| 4,337,041 A | 6/1982 | Harsany | 433/149 |
| 4,696,646 A | 9/1987 | Maitland | 433/149 |
| 4,878,508 A | 11/1989 | Durbin | 132/329 |
| 5,230,263 A | 7/1993 | Kwaka | 81/125.1 |
| 5,421,725 A | * 6/1995 | Von Weissenfluh | 433/149 |
| 5,448,932 A | 9/1995 | Zurbuchen et al. | 81/124.4 |
| 5,527,181 A | * 6/1996 | Rawls et al. | 433/149 |
| 5,743,738 A | * 4/1998 | Baffelli et al. | 433/149 |
| 5,836,767 A | 11/1998 | Aspel | 433/229 |
| 5,890,900 A | 4/1999 | Fischer et al. | 433/149 |
| 5,890,901 A | 4/1999 | Fischer et al. | 433/149 |
| 6,142,781 A | 11/2000 | Fischer | 433/149 |
| 6,234,793 B1 | 5/2001 | Brattesamo et al. | 433/39 |

\* cited by examiner

*Primary Examiner*—Ralph A. Lewis
(74) *Attorney, Agent, or Firm*—Workman, Nydegger, Seeley (57) ABSTRACT

The invention generally provides for a dental wedge with elastomeric sides. The body of the dental wedge comprises a head and a tip and generally tapers from the head to the tip. The body of the dental wedge also comprises recessed or mounting surfaces located on each side of the tapered body. Layers, strips, or other forms of elastomeric material are affixed to each of the mounting surfaces. When the dental wedge is inserted between adjacent teeth, the layers of elastomeric material are compressed between the teeth and the body of the dental wedge in such as way as to conform to the contours and irregularities of the tooth surfaces. This generally increases the friction that is applied between the dental wedge and the teeth, thereby providing the dental wedge with increased retention capabilities for remaining in place. The dental wedge can also hold a form against a tooth.

19 Claims, 5 Drawing Sheets

DENTAL WEDGE WITH ELASTOMERIC SIDES FOR ENHANCED RETENTION

RELATED APPLICATIONS

This application is a continuation-in-part of U.S. patent application Ser. No. 09/707,183, entitled "Dental Wedges Having Proximal Ends With Gritty Top Layers," filed Mar. 19, 2001, which is incorporated herein by reference.

BACKGROUND OF THE INVENTION

1. The Field of the Invention

The present invention is in the field of dental retention devices. In particular, the present invention relates to dental wedges that are used for separating teeth and for holding matrix bands against teeth during dental procedures. Even more particularly, the present invention relates to dental wedges comprising elastomeric sides.

2. The Prior State of the Art

In the field of dentistry, dental practitioners often treat patients who have developed cavities in teeth. In order to treat cavities the dental practitioner removes the infected portion of the tooth and then deposits a filling material such as a composite, a resinous material, or an amalgam into the tooth preparation.

During the dental filling procedure, a matrix band is typically placed against the side of the tooth to keep the filling material within the tooth preparation from flowing beyond the desired boundary of the restored tooth. A matrix band typically comprises a thin metallic or plastic strip that is flexible and can be bent around the tooth being restored. If the matrix band is not properly held in place then the filling may be expressed beyond the tooth preparation, thereby distorting the configuration of the restored tooth and possibly causing ledges or overhangs, which can be problematic to adjacent tissues and inhibit cleaning.

An improper filling can lead to dental discomfort, misalignment of teeth, capture of food particles, infections, and other dental problems. To avoid these problems, and to fix a distorted dental filling, it may be necessary to grind or drill the filling material down to the proper shape, or even replace the filling entirely. It is desirable to avoid this process because it can increase the time and expense of restoring the tooth and can also create anxiety and discomfort for the patient being treated. Accordingly, it is desirable to keep the matrix band in proper placement during the filling procedure so that the dental filling material molds into a shape that approximates the desired shape of the restored tooth and fits precisely.

In order to hold the matrix band in a desired placement, small dental wedges are often placed in the interproximal spaces between the matrix band and the adjacent tooth. Sometimes, dental wedges are also used to separate the teeth to make room to accommodate, or to compensate for, the thickness of the matrix band between the teeth. Existing dental wedges are typically composed of a wood or semi-rigid plastic material having properties that enable the dental wedge to be slightly deformed while maintaining a sufficiently rigid or semi-rigid structure. These properties generally enable the dental wedge to force teeth apart without damaging the teeth. After the dental wedge is removed the compressed periodontal fibers return to their original dimension and cause the displaced teeth to return to their designated positions.

One inherent problem with the use of dental wedges, however, is that they are prone to slipping out from between the teeth during the dental procedure because the frictional forces holding the dental wedges in place are not adequate. Additionally, existing dental wedges are particularly susceptible to slipping out of place because they are generally incapable of conforming to and accommodating the irregularities of, and between, the teeth. They therefore make only limited contact with the teeth, thereby further limiting the frictional forces necessary to hold the dental wedges in place. This is particularly problematic when the surfaces of the dental wedges become wet and slippery from the patient's saliva or blood, thereby further decreasing the friction that is applied over this limited area of contact between the dental wedges and the surfaces of the teeth.

One attempt to address the problems associates with rigid wedges is the FLEXI-WEDGE, which is made from a semi-rigid plastic material and which has a generally upside-down V-shaped cross section. This makes it capable of flexing along its base as it is forced between teeth. Nevertheless, the FLEXI-WEDGE also suffers from an inability to accommodate and conform to irregularities of, and between, the teeth.

Accordingly, there is currently a need in the art for an improved dental wedge with improved retention capabilities for remaining in place within the interproximal space between teeth, for spacing teeth apart, and for hold matrix bands in proper placement during dental procedures.

SUMMARY OF THE INVENTION

The present invention is directed to improved dental wedges for use in dental procedures. In particular, dental wedges of the invention have retention capabilities that help the dental wedges stay in place when inserted between adjacent teeth.

In one presently preferred embodiment, a dental wedge of the invention comprises a tapered body that is configured to be inserted within the interproximal space between two adjacent teeth. The body comprises a head and a tip and generally tapers from the head to the tip.

The body of the dental wedge also comprises recessed mounting surfaces located on each side of the tapered body. Layers, strips, or other forms of elastomeric material are affixed to each of the recessed mounting surfaces. When the dental wedge is inserted between adjacent teeth, the strips of elastomeric material become compressed as needed between the teeth and the body of the dental wedge. As the strips of elastomeric material are compressed, they bulge out and extend beyond the surfaces of the teeth against which they are compressed. This increases the surface area over which friction is applied and also causes the dental wedge to apply multi-directional forces to the surfaces of the teeth, thereby holding the dental wedge in place and keeping the dental wedge from slipping out from between the teeth. To further increase the frictional forces holding the dental wedge in place, the elastomeric sides may be textured, such as with a gritty surface.

The present invention contemplates the use of elastomeric materials that are completely resilient, i.e., materials that will spring back to their original shape after being deformed. On the other hand, it may be desirable, in some cases, to utilize an elastomeric material that is not entirely resilient but which exhibits some degree of semi-set or deformation memory. This allows the wedge to be deformed during placement to a desired degree without the resiliency of elastomer thereafter substantially increasing the level of spreading force between the teeth while still being able to rebound enough to conform to the irregularities of, and between, the teeth. Conforming to the irregularities of the teeth not only increases the frictional force between the wedge and teeth but also helps to prevent the dental filling material from expressing into gaps associated with the irregularities prior to setting.

In one preferred embodiment, the elastomeric material comprises a thermoplastic elastomer. It should be appreciated, however, that the elastomeric material can comprise any substance having elastomeric properties. Other suitable elastomers include, but are not limited to rubber, silicone, latex, chemical set and thermoset elastomers, and equivalents. The strips of elastomeric material that are deposited on the tapered body can also vary in thickness in order to alter the retention capabilities of the dental wedge. For example, the elastomeric material may be deposited in greater thickness near the tip or center portions of the dental wedge, or they may follow the same contours as conventional wedges that are not elastomeric. They may be convex, concave or irregular so as to accommodate any desired situation.

The elastomeric material can be affixed to the body of the dental wedge by any suitable process, such as by casting or co-molding together with the other structural components of the dental wedge. The elastomeric material can also be manufactured separately from the body and subsequently affixed to the body with any suitable attachment means, such as with ultrasonic welding, friction welding, adhesives, glues, epoxies, and cements.

The benefits, features and advantages of the dental wedges of the present invention will become more fully apparent from the following description and appended claims, or may be learned by practicing the invention as set forth below.

BRIEF DESCRIPTION OF THE DRAWINGS

A more extensive description of the present invention, including the above-recited features and advantages, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which:

FIG. 7 also illustrates a second dental wedge inserted between two of the three teeth with elastomeric sides that are conforming to the contours and irregularities of the teeth.

DETAILED DESCRIPTION OF THE PREFERRED EMBODIMENTS

The present invention relates to improved dental wedges, more particularly, to dental wedges having elastomeric sides that provide improved retention capabilities for keeping the dental wedges in place within the interproximal spaces between adjacent teeth.

Figure 1:
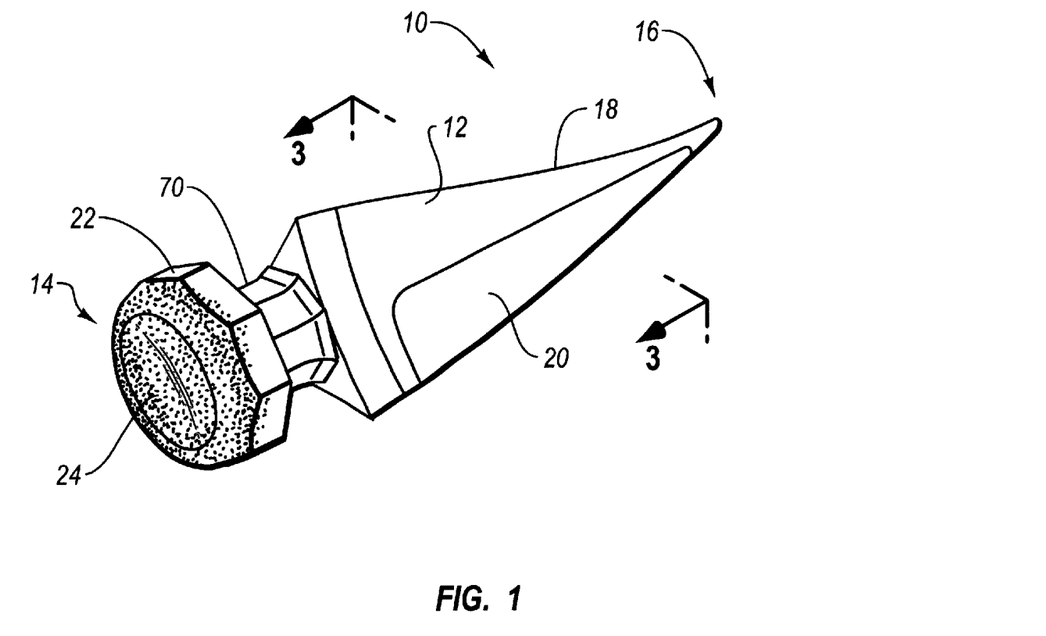
FIG. 1 is a top perspective view illustrating a dental wedge according to the present invention, including a head, a tip, a tapered body that generally tapers from the head to the tip, and a strip of an elastomeric material affixed to the tapered body.

FIG. 1 illustrates a presently preferred embodiment of a dental wedge of the invention. As shown, dental wedge 10 comprises a body 12 extending from a proximal end 14 to a distal end 16. As depicted, proximal end 14 can have an octagonal shaped head 22 to facilitate gripping of the dental wedge 10, using fingers, pliers or other appropriate instruments. This embodiment is useful for enabling dental practitioners to insert dental wedge 10 into the interproximal space between adjacent teeth at various angles, if needed. It should be appreciated that the shape of proximal end 14 and head 22 can vary in size and shape and is not limited to the octagonal shape shown in FIG. 1.

According to the present embodiment, head 22 also comprises a face 24 that is preferably textured and concaved. The concaved shape and texture of face 24 is useful for overcoming a common problem with existing dental wedges, in which tools that are used to push the dental wedges into the interproximal spaces between teeth are susceptible to slipping off of the dental wedges while applying a force to the dental wedges. This is a problem because the tool can potentially cause damage to teeth and sensitive mouth tissue when they slip off of the dental wedges. The present embodiment of the invention overcomes this problem by providing a contour and texture to face 24 that helps to prevent tools from slipping off of the face 24 while applying a force to dental wedge 10.

Other benefits and features of texturing the proximal end of a dental wedge are described in U.S. patent application Ser. No. 09/707/183, filed Mar. 19, 2001, and entitled "Dental Wedges Having Proximal Ends With Gritty Top Layers," which is incorporated herein by reference.

Figure 2:
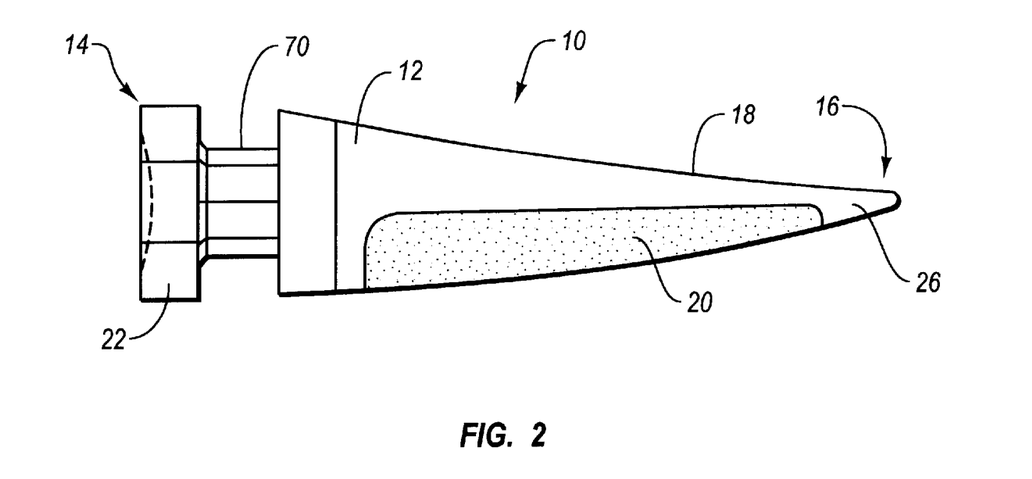
FIG. 2 is a side view of the dental wedge of FIG. 1 that shows the tapered body of the dental wedge tapering from the head down to the tip.

FIG. 2 is a side view of dental wedge 10 of the present embodiment. As shown, body 12 tapers from proximal end 14 to distal end 16, such that distal end 16 comprises a tip 26. As shown, tip 26 is somewhat bulbous or blunt, which is useful in certain circumstances because the bulbous or blunt shape makes tip 26 less likely to pierce sensitive mouth tissue than a sharply pointed tip. It should be appreciated, however, that tip 26 can be configured into any suitable shape. For example, tip 26 can also be sharply pointed to facilitate the insertion of dental wedge 10 into very narrow interproximal spaces between teeth. When tip 26 is sharply pointed, it may be useful to coat tip 26 with elastomeric material so as to provide a cushion that can help prevent tip 26 from damaging sensitive mouth tissue.

According to one embodiment, body 12 is composed of a substantially rigid material. Suitable materials for body 12 may include, but are not limited to plastics, woods, metals, and ceramics. According to one embodiment, body 12 is composed of a thermoplastic or thermoset material and may be formed by injection molding or casting. The rigidity of body 12 enables dental wedge 10 to separate adjacent teeth when body 12 is inserted between the teeth. The further dental wedge 10 is inserted between the teeth, the more the teeth will be separated.

Typically, when teeth are separated with a dental wedge, periodontal fibers attached to the teeth apply a countervailing force that pulls the teeth back together. This force is transferred from the teeth to the dental wedge and tends to urge the dental wedge from out from between the teeth. This is an inherent problem with existing dental wedges of the prior art, in that they are susceptible to slipping out from between the teeth.

The dental wedges of the present invention overcome this problem by providing a rigid inner body 12 with elastomeric outer sides 18 and 20. The rigid inner body 12 generally enables the dental wedges 10 to separate adjacent teeth while the elastomeric outer sides 18 and 20 generally provide the retention capabilities for overcoming the forces that are generated by the periodontal fibers, thereby enabling the dental wedges 10 of the invention to remain in place within the interproximal spaces between adjacent teeth while conforming to the irregularities and contours of the teeth. Conforming to the irregularities of the teeth not only increases the frictional force between the dental wedge 10 and teeth but also helps to prevent the dental filling material from expressing into gaps associated with the irregularities prior to setting. To further increase the frictional forces holding the dental wedge 10 in place, the elastomeric sides 18 and 20 may also be textured, such as with a gritty surface, as illustrated in FIG. 2.

The present invention contemplates the use of elastomeric materials that are completely resilient, i.e., materials that will spring back to their original shape after being deformed. On the other hand, it may be desirable, in some cases, to utilize an elastomeric material that is not entirely resilient but which exhibits some degree of semi-set or deformation memory. This allows the wedge to be deformed during placement to a desired degree without the resiliency of elastomer thereafter substantially increasing the level of spreading force between the teeth while still being able to rebound enough to conform to the irregularities of, and between, the teeth. According to the present embodiment, the elastomeric sides comprise one or more strips of elastomeric material affixed to the body 12 of the dental wedge 10. Suitable elastomeric material may include, but is not limited to rubber, silicone, latex, elastic, chemical set and thermoset plastics.

It should be appreciated that although the dental wedge of the invention is useful for separating teeth, the width of the body 12 may vary to accommodate different needs and purposes. For example, in one alternative embodiment, the body 12 of the dental wedge 10 is very narrow, so as to not further separate the teeth, but is provided for supporting the elastomeric sides 18 and 20. This embodiment is useful, for example, for pushing and holding a matrix band conformingly in place against the surface of a tooth without further separating the teeth.

Figure 3:
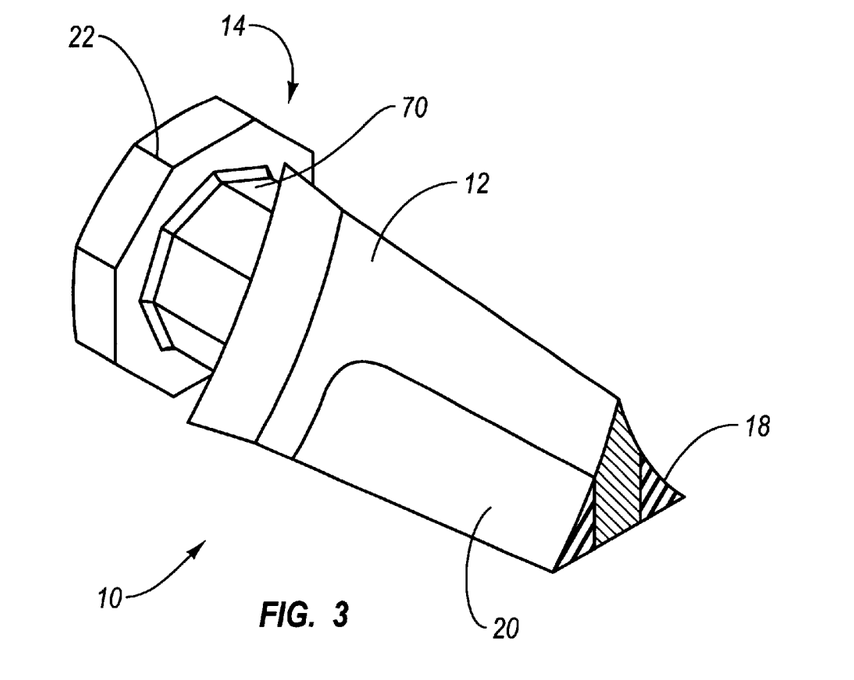
FIG. 3 is a top perspective cross-sectional view of the dental wedge of FIG. 1 taken along line 3—3 showing strips of elastomeric material affixed to opposite sides of the tapered body.

FIG. 3 is a cross-sectional view 3—3 of FIG. 1 that better depicts elastomeric sides 18 and 20 affixed to rigid body 12 of dental wedge 10. Elastomeric sides 18 and 20 can be affixed to body 12 by any suitable means. By way of example and not limitation, elastomeric sides 18 and 20 can be co-molded or cast onto body 12. Elastomeric sides 18 and 20 may also be manufactured independently and subsequently connected to body 12 by, e.g., ultrasonic welding, friction welding, adhesives, glues, epoxies, or cements.

Although FIG. 3 shows elastomeric sides 18 and 20 having a cross-sectional area that is substantially triangular, it should be appreciated that the size and shape of elastomeric sides 18 and 20 can vary without departing from the spirit of the invention. For example, the cross-sectional area of elastomeric sides 18 and 20 can also be rectilinear, angular, or curved.

Elastomeric sides 18 and 20 can vary in thickness and material properties for providing different compression, adhesion, and retention capabilities to dental wedge 10 and for enabling the dental wedge 10 to conform to different magnitudes of irregularities and curvatures of the teeth. According to one alternative embodiment, elastomeric sides 18 and comprise multiple layers of elastomeric material, with each layer possessing different elastomeric properties.

Figure 4A:
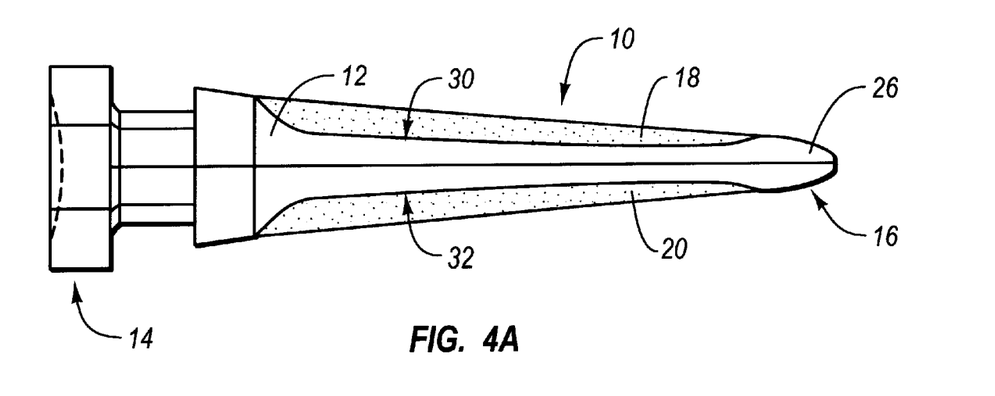
FIG. 4A is a top view illustrating a body of a dental wedge according to the invention having recessed surfaces and straight elastomeric sides deposited on the recessed surfaces.

FIG. 4A illustrates one presently preferred embodiment of rigid body 12 of dental wedge 10 in which body 12 is configured with recessed surfaces 30 and 32 for receiving and mounting strips of elastomeric material comprising elastomeric sides 18 and 20. Although recessed surfaces 30 and 32 are shown to be smooth, it should be appreciated that they can also be textured. Texturing may be desirable in order to improve the bond between surfaces 30 and 32 and the elastomeric material deposited thereon. As described earlier, the width of the body 12 may also vary to accommodate different purposes.

Although certain embodiments show and describe elastomeric material affixed only to the side portions of body 12, it should be appreciated that the elastomeric material of elastomeric sides 18 and 20 can be coated or layered over the entire of dental wedge 10 or over any selected portions of dental wedge 10. Furthermore, although the elastomeric sides 18 and 20 are shown to be straight, it should be appreciated that the elastomeric sides 18 and 20 may also be convex, concave or irregular so as to accommodate any desired situation. For example, the elastomeric material of the elastomeric sides 18 and 20 may be deposited in greater thickness near the tip 26 or center portions of the dental wedge 10.

Figure 4B:
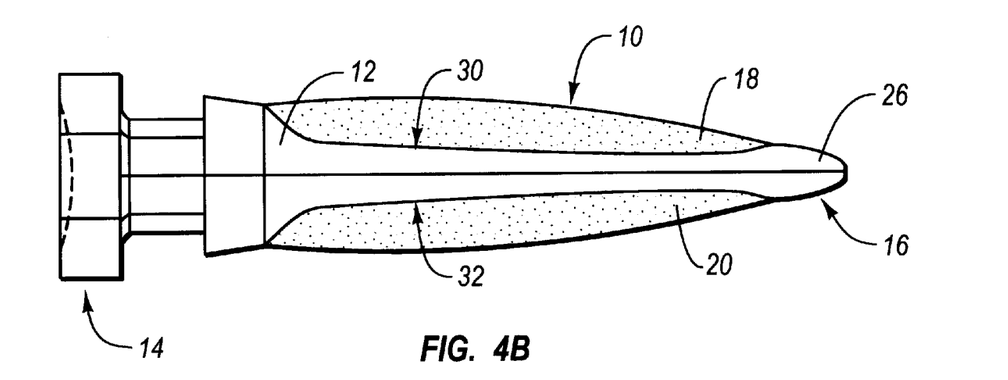
FIG. 4B is a top view illustrating a body of a dental wedge according to the invention having convex elastomeric sides.
Figure 4C:
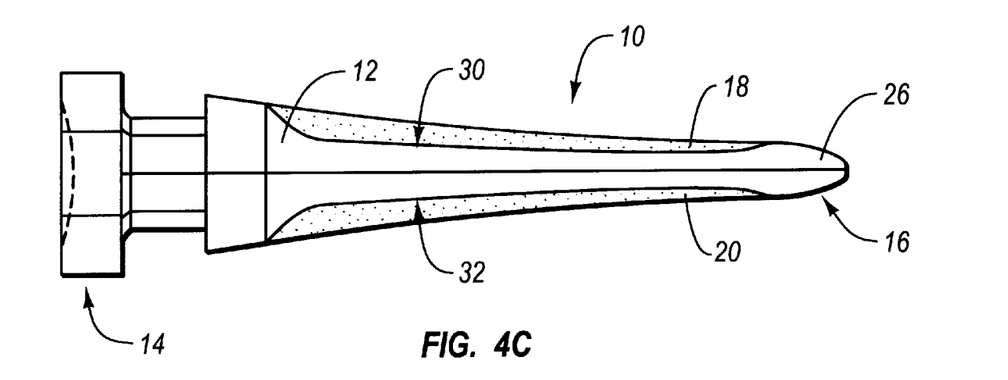
FIG. 4C is a top view illustrating a body of a dental wedge according to the invention having concave elastomeric sides.
Figure 4D:
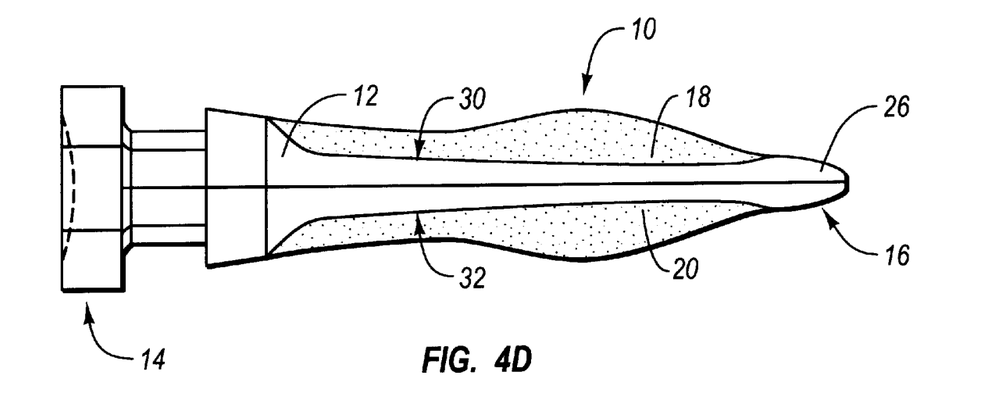
FIG. 4D is a top view illustrating a body of a dental wedge according to the invention having irregular shaped elastomeric sides, with a greater portion of the elastomeric material deposited near the front.

FIG. 4B illustrates one embodiment in which the elastomeric sides 18 and 20 are convex, having more elastomeric material deposited near the center portions of the body 12. This embodiment is useful when there are deep contours or irregularities between the teeth that can conformingly be filled with the elastomeric material. FIG. 4C illustrates one embodiment in which the elastomeric sides 18 and 20 are concave. This embodiment is useful when there are only shallow contours or irregularities between the teeth. FIG. 4D illustrates one embodiment in which the elastomeric sides 18 and 20 are irregularly shaped, with more elastomeric material deposited in greater thickness near the front of the dental wedge 10 to create greater compression and frictional surface area on the innermost interproximal spaces between teeth. This embodiment is particularly useful for providing the dental wedge 10 with additional resistance from slipping out from between the teeth once it is inserted.

Figure 5:
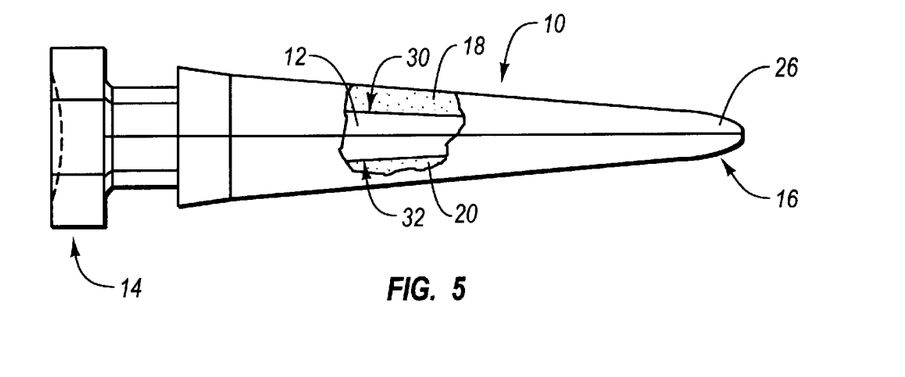
FIG. 5 is a partial cross-sectional top view illustrating a thin wedge-shaped body in which elastomeric material is deposited over the body.

According to yet another embodiment, as shown in FIG. 5, the body 12 of the dental wedge 10 comprises a conventional wedge shape and the elastomeric material is deposited over the entire body 12 of the dental wedge 10. This embodiment may be preferred for ease of manufacture.

Figure 6:
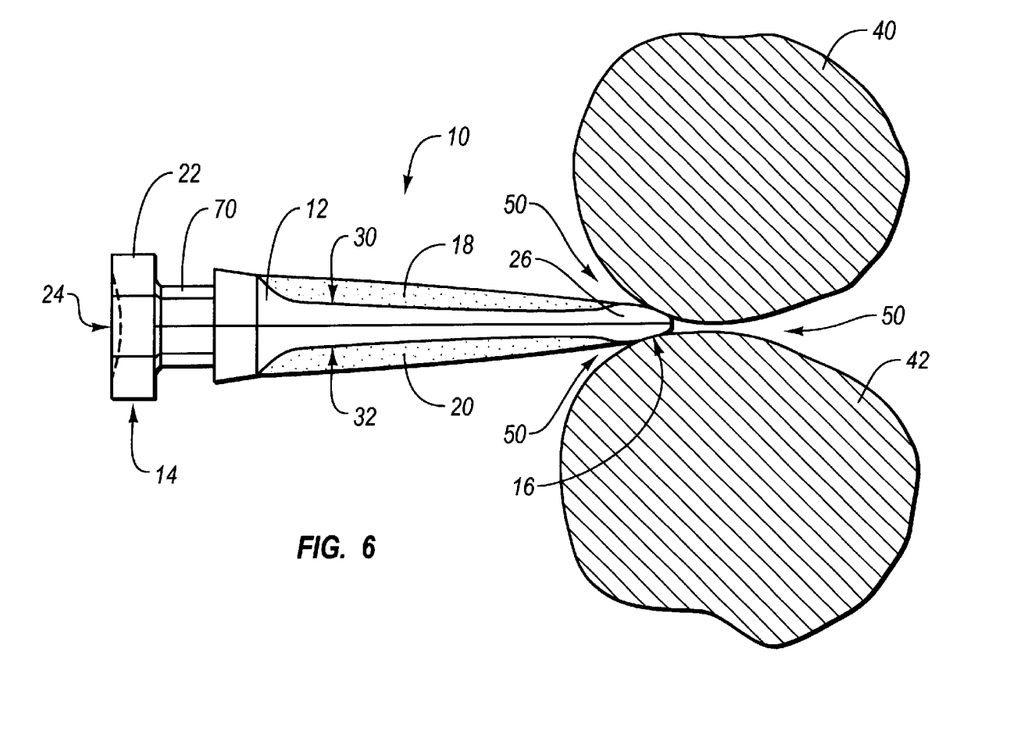
FIG. 6 is a top view of the dental wedge of FIG. 1 with a tip of the dental wedge being inserted between two adjacent teeth.
Figure 7:
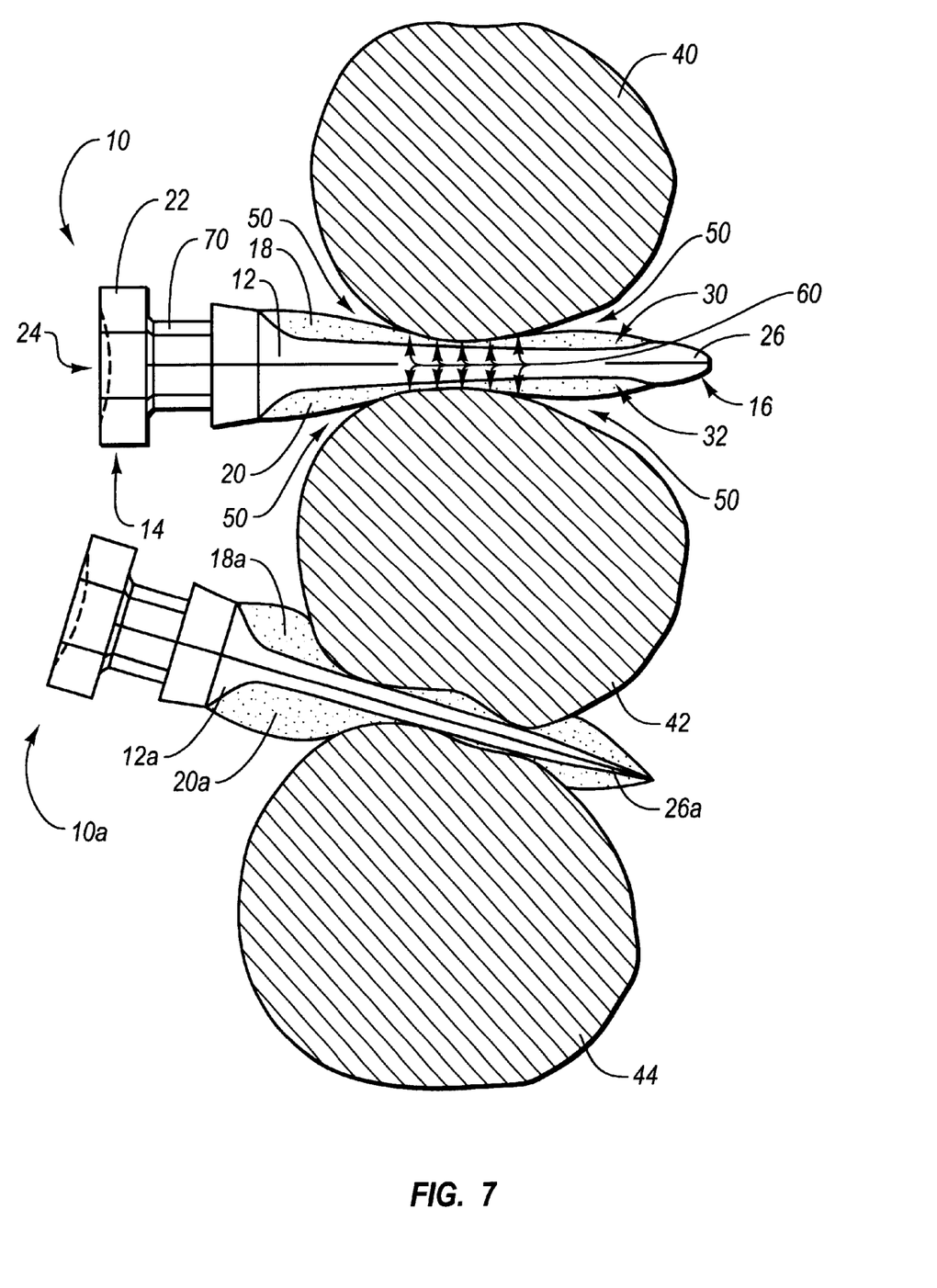
FIG. 7 is a top view of the dental wedge of FIG. 1 inserted between two of three adjacent teeth, with elastomeric sides of the dental wedge compressed between the teeth and the body of the dental wedge.

A preferred method for using the dental wedge of the present invention to separate teeth will now be shown and described in reference to FIGS. 6 and 7.

FIG. 6 is a top cross-sectional view of two adjacent teeth 40 and 42. FIG. 6 also shows one presently preferred embodiment of dental wedge 10 in position to be inserted between teeth 40 and 42, with tip 26 inserted slightly within the interproximal space 50 between teeth 40 and 42. To further separate teeth 40 and 42, tip 26 is inserted into the interproximal space 50 between the teeth 40 and 42, as shown, and a force is applied to the back of dental wedge 10 at the proximal end 14. The force can be applied by pushing directly on the face 24 of the proximal end 14 or by gripping and pushing the head 22 with cotton pliers or another device, as described in reference to FIG. 1. Once an adequate force is applied to proximal end 14, dental wedge 10 will be forced between the teeth 40 and 42, thereby causing the teeth 40 and 42 to separate.

As shown in FIG. 7, once dental wedge 10 has been forced between teeth 40 and 42, elastomeric side 18 is compressed between tooth 40 and rigid body 12, and elastomeric side 20 is compressed between tooth 42 and body 12. This compression causes each of the elastomeric sides 18 and 20 to better conform to the enlarged space between the teeth 40 and 42, and also to deform and bulge outwardly somewhat, thereby increasing the frictional surface area over which dental wedge 10 is in contact with the teeth 40 and 42. It will be appreciated that this directly improves the retention capabilities of dental wedge 10 because friction is applied over the entire area in which dental wedge 10 makes contact with the surfaces of teeth 40 and 42. Essentially, elastomeric sides 18 and 20 conform and adhere to the surfaces of teeth 40 and 42, thereby preventing dental wedge 10 from slipping out from between the teeth 40 and 42. The bulging portion of the elastomeric strips 18 and 20 further help to retain dental wedge 10 in place between teeth 40 and 42.

The deformation of the elastomeric sides 18 and 20 also creates multidirectional forces 60 that improve the retention capabilities of dental wedge 10. Multidirectional forces 60 consist of multiple discrete forces that are distributed over the contact area existing between elastomeric sides 18 and 20 and each of the tooth surfaces. In particular, a discrete force is applied at every point of contact between dental wedge 10 and the surfaces of teeth 40 and 42. Some multidirectional forces 60 are illustrated in FIG. 7. It should be appreciated that multidirectional forces 60 generally increase the friction between dental wedge 10 and teeth 40 and 42, thereby helping to retain dental wedge 10 in place within the interproximal space 50 between tooth 40 and tooth 42. As described above, and as shown, the elastomeric sides 18 and 20 may also be textured to increase the frictional retention forces. When desired, dental wedges 10 can be pulled out from between the teeth 40 and 42 with pliers, fingers, or another device.

FIG. 7 also illustrates a second dental wedge 10a that is inserted between teeth 42 and 44. Second dental wedge 10a is substantially similar to dental wedge 10 except that body 12a is very thin and wedge-shaped with elastomeric sides 18a and 20a extending all the way down to and over tip 26a, which is pointed. Because body 12a is so thin, dental wedge 10a does not cause excessive spacing of the teeth 42 and 44. In some circumstances this is preferred, such as for holding a matrix band form in place. Even without spacing the teeth, elastomeric sides 18a and 20a are able to compress and conform to the surface contours and irregularities of the teeth 42 and 44 and may therefore provide a suitable aid for filling a tooth with a dental filling by preventing the dental filling material from expressing into gaps associated with the irregularities prior to setting. Although dental wedge 10a may be used alone, one skilled in the art will appreciate that the dental wedge 10a is particularly well suited for use in combination with a matrix band for providing form for a dental filling. In particular, dental wedge 10a can securely press against and hold a matrix band against the surface of a tooth, while urging the matrix band to conform to the shape of the tooth, and thereby provide desired form for filling the tooth.

Accordingly, although certain embodiments of the dental wedges of the invention are shown and described as being used for separating teeth, it should be appreciated that uses and applications of the dental wedges of the present invention extend beyond separating teeth. For example, the dental wedges of the invention can be used to hold a matrix band in a desired placement against a tooth, even without separating teeth, by placing a suitable dental wedge of the invention between the matrix band and an adjacent tooth. The dental wedges of the invention can conform to the shape of the teeth, with or without separating the teeth, thereby providing form and support, such as, for example, when holding a matrix band in place against a tooth. Dental wedges of the invention can also be placed between two matrix bands for holding each of the matrix bands against adjacent teeth in desired placements. The benefits and advantages of the present invention extend to these and other applications by providing elastomeric sides that generally enable the dental wedges to maintain a desired position between teeth, while conforming to the shape of the teeth, so as to effectively separate the teeth and/or for holding matrix bands or other similar devices firmly in place against the surfaces of the teeth.

The invention, as it has been described herein, generally provides a dental wedge with elastomeric sides. When the dental wedge is inserted between teeth, it causes the teeth to separate and the elastomeric sides to conform to the surfaces of the separated teeth. The elastomeric sides generally provide increased areas of contact between the dental wedge and the separated teeth and further provide multidirectional forces that are applied to the teeth, thereby providing the dental wedge with increased retention capabilities for remaining in position between the teeth. It should be appreciated that these benefits of the invention are advantages over the prior art.

It should also be appreciated that the present invention may be embodied in other forms without departing from its spirit or essential characteristics. For example, the shape of the body of the dental wedge may vary and the elastomeric material affixed to the dental wedge can cover the entire dental wedge or any selected portions of the dental wedge. Additionally, the elastomeric material can be deposited in varying thickness and patterns over the body of the dental wedge in order to alter the retention capabilities of the dental wedge. For example, the elastomeric material may be deposited in greater thickness near the tip or center portions of the dental wedge to create greater compression and frictional surface area on the innermost interproximal spaces between teeth.

Furthermore, according to other embodiments, as shown in FIGS. 1–7, body 12 of dental wedge 10 may also comprise a recessed neck 70 that facilitates the receipt of prongs of special pliers, such as cotton pliers, or other pulling devices for pulling dental wedge 10 out from between teeth 40 and 42. Neck 70 can also be used for receiving prongs of a tool for pushing dental wedge 10 into the interproximal space between teeth. It should be appreciated, however, that in other embodiments dental wedge 10 does not comprise a neck 70.

Accordingly, the invention is not limited to dental wedges comprising only elastomeric sides. As properly understood, the preceding description of specific embodiments is illustrative only and in no way restrictive. The scope of the invention is, therefore, indicated by the appended claims as follows.

What is claimed and desired to be secured by United States Letters Patent is:

1. A dental wedge for insertion between adjacent teeth of a patient, comprising:
    a substantially rigid body configured to be inserted within an interproximal space between adjacent teeth, wherein said substantially rigid body tapers from a proximal end to distal end; and
    an elastomeric material affixed to a portion of the body, the elastomeric material having a greater thickness in the region of the tapered distal end of the body than at the proximal end of the body.

2. A dental wedge as defined in claim 1, wherein the elastomeric material is configured to conform to the shape of the adjacent teeth upon the dental wedge being inserted between the adjacent teeth.

3. A dental wedge as defined in claim 2, wherein the elastomeric material is further configured to conform to the shape of the adjacent teeth without causing separation of the adjacent teeth.

4. A dental wedge as defined in claim 2, wherein a matrix band is disposed against one of the adjacent teeth, such that when said dental wedge is inserted within the interproximal space the elastomeric material becomes at least partially compressed between the substantially rigid body and the matrix band and holds the matrix band in place while urging the matrix band to conform to the shape of the tooth against which it is disposed.

5. A dental wedge as defined in claim 2, wherein the elastomeric material comprises at least one of rubber, silicone, and latex.

6. A dental wedge as defined in claim 2, wherein the substantially rigid body includes at least two sides and wherein the elastomeric material is affixed to at least a portion of each of said two sides.

7. A dental wedge as defined in claim 2, wherein the proximal end of the substantially rigid body includes a head.

8. A dental wedge as defined in claim 7, wherein the head is configured to facilitate gripping during insertion into and removal of said wedge from an interproximal space between two adjacent teeth.

9. A dental wedge as defined in claim 7, wherein the head includes at least one of a concaved surface and a gritty surface.

10. A dental wedge as defined in claim 1, wherein the elastomeric material is attached as an elastomeric strip.

11. A dental wedge for insertion between adjacent teeth of a patient, comprising:
    a substantially rigid body configured to be inserted within an interproximal space between adjacent teeth, wherein said substantially rigid body comprises a first side and a second side and tapers from a head to a tip;
    an elastomeric material affixed to each of the first and second sides; and
    a gritty material formed on at least a portion of the elastomeric material on at least one of the first and second sides.

12. A dental wedge as defined in claim 11, wherein the elastomeric material is configured to conform to the shape of the adjacent teeth upon the dental wedge being inserted between the adjacent teeth.

13. A dental wedge as defined in claim 11, wherein the elastomeric material comprises multiple layers of elastomeric material, and wherein each layer of elastomeric material has different material properties.

14. A dental wedge as defined in claim 13, wherein each of said multiple layers comprises at least one of a chemical set and a thermal set material.

15. A dental wedge as recited in claim 11, wherein the elastomeric material has a greater thickness in the region of the tip than at the head of the body.

16. A dental wedge as defined in claim 11, wherein the head is configured to facilitate gripping for insertion into and removal of said wedge from an interproximal space between two adjacent teeth.

17. A dental wedge as defined in claim 11, wherein said tip is bulbous.

18. A dental wedge as defined in claim 11, wherein said tip is sharply pointed.

19. A dental wedge as defined in claim 11, wherein said body is substantially wedge-shaped.

* * * * *

UNITED STATES PATENT AND TRADEMARK OFFICE
CERTIFICATE OF CORRECTION

PATENT NO. : 6,402,514 B1
DATED : June 11, 2002
INVENTOR(S) : Dan E. Fischer and Bruce S. McLean Page 1 of 1

It is certified that error appears in the above-identified patent and that said Letters Patent is hereby corrected as shown below:

<u>Title page,</u>
Item [57], ABSTRACT,
Line 10, after "dental wedge in such" change "as" to -- a --

<u>Column 2,</u>
Line 25, after "apart, and for" change "hold" to -- holding --

<u>Column 4,</u>
Line 53, after "Ser. No." change "09/707/183" to -- 09/707,183 --

Signed and Sealed this

Eighteenth Day of February, 2003

JAMES E. ROGAN
*Director of the United States Patent and Trademark Office*